United States Patent [19]

Mayer

[11] 4,350,246

[45] Sep. 21, 1982

[54] RELEASABLE SURGICAL PRODUCTS AND PROCESS OF FORMATION THEREOF

[75] Inventor: Nathan Mayer, East Brunswick, N.J.

[73] Assignee: The Hartford Corporation, New Brunswick, N.J.

[21] Appl. No.: 141,814

[22] Filed: Apr. 21, 1980

[51] Int. Cl.³ .................... A61B 17/06; A61L 15/00
[52] U.S. Cl. .................................. 206/210; 206/440; 206/494; 428/906
[58] Field of Search ............... 206/210, 440, 494; 428/906

[56] References Cited

U.S. PATENT DOCUMENTS

| | | | |
|---|---|---|---|
| 3,085,921 | 4/1963 | Zeise, Jr. | 428/906 |
| 3,349,765 | 10/1967 | Blanford | 206/440 |
| 3,364,928 | 1/1968 | Creager, Jr. et al. | |
| 3,509,991 | 5/1970 | Horst | 428/906 |
| 3,553,074 | 1/1971 | Knepp | 428/906 |
| 3,613,675 | 10/1971 | Endres et al. | |
| 3,625,205 | 12/1971 | Madden et al. | |
| 3,654,064 | 4/1972 | Laumann | 428/906 |
| 3,823,057 | 7/1974 | Roberts et al. | 428/906 |
| 3,879,257 | 4/1975 | Gentile et al. | 162/112 |
| 3,916,447 | 11/1975 | Thompson | 428/906 |
| 3,916,887 | 11/1975 | Kelly . | |
| 3,928,690 | 12/1975 | Settineri et al. | 428/906 |
| 4,027,665 | 6/1977 | Scrivens . | |
| 4,189,514 | 2/1980 | Johnson | 428/906 |
| 4,258,092 | 3/1981 | Labar | 428/906 |

Primary Examiner—Joseph Man-Fu Moy
Attorney, Agent, or Firm—Philip H. Gottfried

[57] ABSTRACT

A process for specially treating the surfaces of absorbent fibrous surgical products such as towels, surgical drapes and the like. After the subject treatment, the products formed can be folded, stacked and packaged without appreciable fiber entanglement developing between contiguous surfaces of the products. Importantly, the products can be subjected to sterilizing radiation while folded in their package, and may thereafter be readily unfolded without sticking or blocking as might otherwise result from the exposure to sterilizing radiation.

5 Claims, 7 Drawing Figures

RELEASABLE SURGICAL PRODUCTS AND PROCESS OF FORMATION THEREOF

DESCRIPTION OF THE INVENTION

The present invention relates generally to a surface treatment process and the product formed, and more particularly to a process for specially treating the surfaces of absorbent fibrous surgical products with a release agent to avoid sticking or blocking between contiguous surfaces of the products after they are folded, packaged and radiation sterilized.

Disposable surgical products such as towels, surgical drapes, gowns and the like have become widely accepted and are preferred over equivalent cloth products which require laundering and sterilization after each use. These disposable products are usually made from paper fibers that provide softness, strength and absorbency comparable to that obtained with comparable cloth products. For example, U.S. Pat. No. 3,879,257 discloses a unitary fibrous web construction, the fibers being bound together by an elastomeric material which is typically applied to the web in a lattice pattern. Fiber areas are left exposed within the pattern of binder material so that moisture absorption by the web fibers is maintained when the web is used in the manufacture of disposable surgical products.

Surgical products formed of a fibrous material, such as those disclosed in U.S. Pat. No. 3,879,257 discussed hereinbefore, are normally supplied in a folded configuration (sometimes referred to as "W" folded). In such a configuration, when the topmost product of a stack of such products is removed from the stack, it should readily unfold by its own weight into a fully opened configuration. It is commonplace to sterilize closed packages of such surgical products by exposure thereof to cobalt radiation to ensure asepsis thereof when the products are put to use, for example, in an operating room.

Unfortunately, a problem has arisen in connection with the folding, packaging and sterilization of surgical products made from webs of fibrous material, particularly when the web has a binder material present on its surface. Specifically, contiguous surfaces of the folded products have frequently been known to stick to one another, thus prolonging the time of their unfolding when each product is taken up from a stack as it is about to be used. Usually, in an operating room situation, a nurse uses a forceps to grab a folded tab on the product to lift it. In the case of a towel, for example, it should be fully opened as it is being handed to a surgeon who has just washed and is ready to dry his hands and arms. The surgeon uses one side of the towel to dry one arm, the other side of the towel to dry the other arm. Thus, the full opening of the towel is critical to this procedure; and, if the towel fails to fully open, it is discarded and a succession of new towels are taken until one opens correctly.

The sticking or blocking problem arises as a result of two factors. First, there is a certain amount of fiber entanglement between exposed fibers on the respective contiguous surfaces of the folded product. It has been found that such entanglement arises in response to even modest pressure applied against the folded surfaces. Thus, in a given stack of the products, the bottom layers may have their folded surfaces entangled merely by the weight of the upper layers in the stack.

Blocking of the folded products also has been known to occur as a result of exposure to cobalt radiation for sterilization purposes. When a fibrous web such as that disclosed in the hereinbefore noted U.S. Pat. No. 3,879,257 is used, for example, the pattern of elastomeric binder present on its surface will at least partially contact itself when the product is folded and packaged. After such packaged product is radiation sterilized, it has been found that the degree of blocking which occurs is even greater than that which would ordinarily result from the fiber entanglement alone. One possible explanation for this phenomenon is that the radiation exposure causes a cross-linking between the binder which then contacts itself between contiguous surfaces of the folded product, the binder typically being an elastomeric polymer.

It is an object of the present invention to overcome the above and other shortcomings in disposable surgical products which are packaged in a folded condition.

It is another object of the present invention to provide a process for treating the surfaces of disposable surgical products so that contiguous surfaces thereof readily separate from one another after the products have been stored in a folded and packaged condition.

It is yet another object of the present invention to provide disposable surgical products which can be packaged in a folded condition and radiation sterilized, without causing blocking or sticking of the products when they are later unfolded to be used.

In accordance with the present invention, a process for treating the surface of a moisture absorbent web of fibrous sheet material having a binder on its surface in a first given pattern includes the step of applying a release agent on a portion of the binder, thereby reducing blocking between contiguous surfaces of the material when the material is folded and exposed to sterilization radiation.

A surgical product in accordance with the present invention, wherein the product is of the kind which is folded to be packaged and then radiation sterilized, comprises a moisture absorbent web of fibrous sheet material having a binder present on its surface in a first given pattern so that fibers of the material are exposed at given areas adjacent the first given pattern. The web also has a release agent applied to its surface in a second given pattern which overlies a portion of the binder and a portion of the fibers exposed at said given areas.

The above brief description, as well as further objects, features and advantages of the present invention will be more fully understood by reference to the following detailed description of the presently preferred, but nonetheless illustrative embodiment, in accordance with the present invention, when taken in conjunction with the accompanying drawing, wherein.

Figure 1:
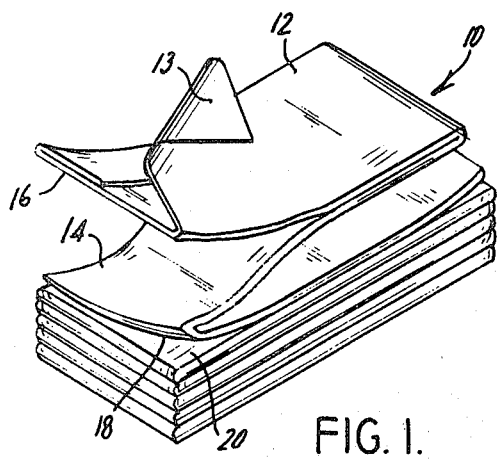
FIG. 1 is a perspective view of a stack of conventionally folded disposable surgical towels, the towels tending to stick together as they are lifted from the stack.
Figure 2:
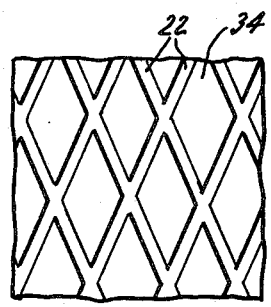
FIG. 2 is an enlarged partial top plan view of a pattern of binder material present on the surfaces of the towels of FIG. 1.

Referring now in detail to the drawing, and initially to FIG. 1 thereof, there is shown a stack 10 of folded, disposable surgical towels, with the topmost towel 12 being lifted away from the stack 10 by way of a folded tab 13. Towel 12 exhibits sticking between its contiguous folded surfaces 14 and 16, as well as between its bottom surface 18 and the top surface 20 of the next lower towel in the stack 10. As discussed above, this sticking problem can arise from entanglement of fibers exposed on the contiguous surfaces 14, 16 and 18, 20, respectively. Also, if the towel 12 has a polymeric binder present on its outer surfaces, as shown at 22 in FIG. 2, the sticking or blocking illustrated in FIG. 1 may arise from cross-linking of the binder on the contiguous surfaces when the towel stack 10 is radiation sterilized after folding and packaging thereof.

Figure 3:
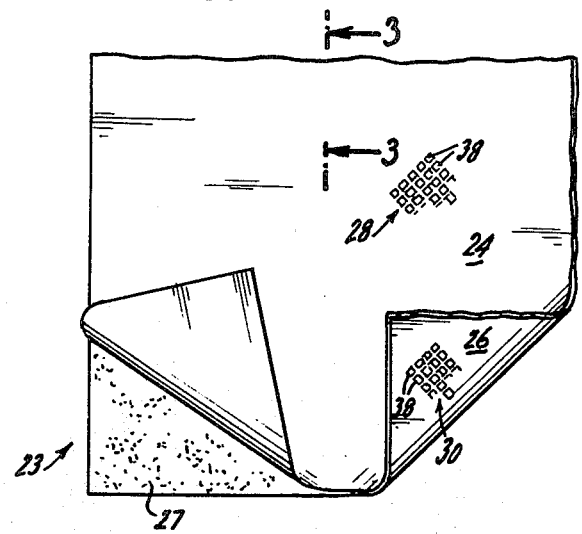
FIG. 3 is a partial top plan view of a two-ply laminate of absorbent fibrous material, showing a release agent deposited on the outer surface of the plies, and an adhesive layer between the plies, in accordance with the present invention.

FIG. 3 shows a portion of a two-ply laminate 23 which is composed of plies 24, 26 of absorbent fibrous sheet material, the plies being bonded together with a conventional adhesive layer 27. In accordance with the present invention, each of the plies 24, 26 has a release agent applied to its outer surface in a particular given pattern. Portions of these patterns are represented at 28 and 30, for illustrative purposes. Also, each of the plies 24, 26 may be supplied with the binder 22 present on its outer surface in the lattice pattern of FIG. 2. This pattern of binder leaves exposed a number of fiber areas 34 on the outer surfaces of the plies 24, 26, adjacent the binder.

Figure 4:
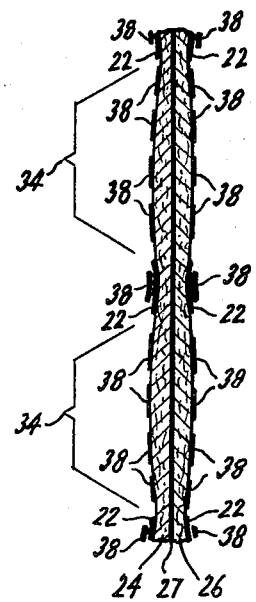
FIG. 4 is a cross-sectional view through the plies of the laminate of FIG. 3 taken substantially along line 4—4 and looking in the direction of the arrows, showing the deposits of the release agent extending over exposed fiber areas and over the binder material on the surfaces of each of the plies.

Referring now to FIG. 4, the release agent is deposited in a particular given pattern so that some deposits 38 will lie on portions of the exposed fiber areas 34, and others of the deposits 38 will overlie the binder 22. However, a sufficient quantity of fibers are left exposed within the areas 34 so that the moisture absorbency of the plies 24, 26 is substantially preserved over a relatively short period of time.

Figure 5:
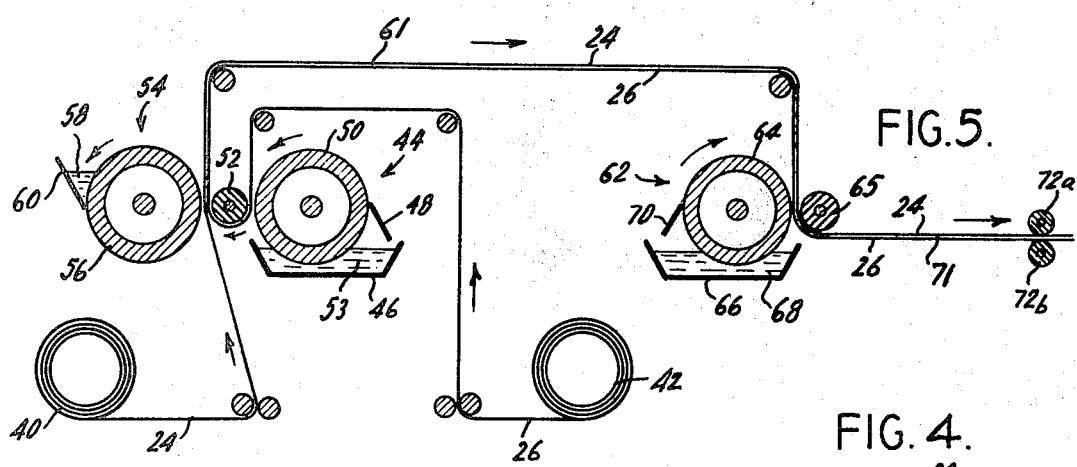
FIG. 5 is a schematic elevational view illustrating a process for making a laminate of the plies shown in FIGS. 3 and 4.

FIG. 5 illustrates a process for producing the two-ply laminate 23 of FIG. 3, in accordance with the present invention. The plies 24, 26 forming the laminate 23 are unwound from separate supply rolls 40 and 42, respectively. These plies each consist of a web of absorbent, fibrous sheet material, which may be the same as or equivalent to that of the sheet material disclosed in U.S. Pat. No. 3,879,257 mentioned hereinbefore, and which is normally supplied with an elastomeric polymeric binder present on one or both of its surfaces. The binder may define a surface pattern which as the lattice of FIG. 2, or any other pattern wherein areas of fiber are left exposed on the surface to absorb moisture.

Ply 26 is guided to an adhesive application station 44 which includes a trough 46, doctor blade 48, an applicator roll 50 and a rubber impression roll 52. Roll 50 may be engraved on its surface so as to transfer a conventional adhesive composition 53 within trough 46 to one side of ply 26.

Figure 6:
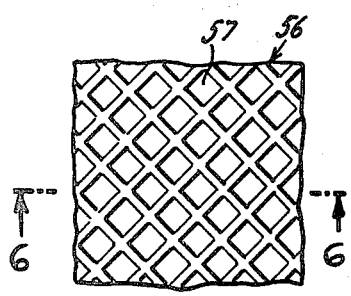
FIG. 6 is an enlarged partial view of a surface pattern engraved in an applicator roller used in the process of FIG. 5; and, FIG. 7 is a cross-sectional view of the engraved pattern taken substantially along line 7—7 in FIG. 5 and looking in the direction of the arrows.
Figure 7:

Ply 24 is brought from supply roll 40 toward a release agent applicator station 54. Station 54 includes an applicator roll 56 which has a particular diamond cellular pattern 57 engraved in its surface. A regular diamond cellular pattern 57 for depositing a release agent in a corresponding pattern on ply 24 is illustrated in FIGS. 6 and 7. A range of from about 75 to about 180 cells per lineal inch has been found suitable for the roll pattern when a silicone solution is used as the release agent.

A solution 58 of the release agent is supplied to the applicator roll 56 downstream from a doctor blade 60, to be transferred by roll 56 onto the outside surface of ply 24. Solution 58 may comprise from about 50 to about 98 percent water, and from about 2 to about 50 percent silicone. An example of a suitable release agent mixture is 90 percent water, 10 percent Dow Corning No. 36 water phase silicone, in conjunction with the use of an applicator roll 56 having 150 cells per lineal inch. This will cause about one-half pound of silicone per ream (3,000 sq. ft.) to be deposited on the outer surface of ply 24 as it is advanced from the nip of impression roll 52 and applicator roll 56.

Impression roll 52 also brings ply 26, with the adhesive coating on its inner surface, against the inner surface of ply 24 to form a two-ply laminate 61. The laminate 61 is advanced toward another release agent applicator station 62, which includes an applicator roll 64, rubber impression roll 65, a trough 66 for containing a release agent solution 68, and a doctor blade 70. The roll 64 and solution 68 may be identical to the roll 46 and solution 58, respectively, at applicator station 54. Accordingly, the release agent solution is applied on the outside surface of ply 26 as the two-ply laminate 61 is advanced from the nip of impression roll 65 and applicator roll 64.

In accordance with the above process, a two-ply laminate of absorbent, fibrous material 71 is provided which has uniform patterns of the release agent solution applied on each of its outside surfaces. The laminate 71 is then carried between hot rolls 72a, 72b to remove the water from the solution. After the laminate 71 is dried so that the pattern of deposits 38 of the release agent remains on its outside surfaces, it may be cut into any desired form such as a surgical towel, drape or the like, folded and then packaged. A stack of such products within a single package may subsequently be exposed to cobalt or other radiation for sterilization purposes and, when one of the products is removed from the package, it will open freely with no tendency to block or stick.

As an example, plies 24, 26 of "Hi-Loft" material were used having the binder 22 present on their outside surfaces in a lattice pattern. Each lattice cell was about 80 by 60 mils. in size, and the width of the pattern lines was about 10 mils. A release agent solution comprising 10 percent Dow Corning No. 36, water phase silicone, and 90 percent water was deposited in a regular diamond pattern, such as represented at 28 and 30 in FIG. 3, with each deposit 38 being about 5 mils. on a side so as to provide about 22,500 deposits 38 per square inch. This procedure substantially reduced sticking or blocking after the finished laminate 23 was folded, subjected to pressure and radiation sterilized. Also, short term moisture absorbency (10–15 sec.) was reduced by only about 12 percent, and long term absorbency (after about one minute) was unaffected. In this example, the silicone deposits 38 overlie about 70 percent of the entire surface areas of each ply, and about 16 percent of the binder present on each ply surface.

Without intending to be limited by any particular theoretical explanations, it is believed that blocking induced by radiation is substantially reduced because of the presence of the release agent deposits 38 directly on the binder 22. This prevents the binder from extensively cross-linking with itself when the plies are folded and then subjected to sterilizing radiation.

Using the "Hi-Loft" plies 24, 26 and the silicone release agent solution of the previous example, it has been found that the release agent can be deposited so as to overlie from about 45 up to about 90 percent of the entire ply surface areas to obtain a significant reduction in radiation induced blocking, without seriously affecting the moisture absorption characteristics of the plies. This range of allowable surface coverage corresponds to coverage of from about 15 to about 18 percent of the area of the binder pattern present on the ply surface.

It is also preferred that no substantial residue remain on the ply surfaces after the release agent solution is deposited thereon and heated to dry. Thus, a silicone water solution such as that of the previous example has proven to be satisfactory, while others including solvents such as Methyl Ethyl Ketone have been found to leave a residue after drying which impairs the effectiveness of the release agent in overcoming the blocking and sticking problems.

It should also be noted that the depositing of a silicone release agent on surgical towels, according to the present invention, provides the added benefit of relieving a surgeon's hands from irritation and strain such as may be encountered during an operating procedure.

As will be readily apparent to those skilled in the art, the present invention may be practiced in other specific forms and for other purposes without departing from its spirit or essential characteristics. For example, the binder may be present on the ply surfaces in other than lattice like patterns, and the pattern of deposits 38 of the release agent made on the ply surfaces need not be in a diamond form, as shown. Hence, both of these patterns may vary in size and form, yet radiation induced blocking will still be alleviated provided the deposits 38 cover a portion of the binder.

The present embodiment is, therefore, to be considered as illustrative and not restrictive, the scope of the invention being indicated by the claims rather than by the foregoing description, and all changes which come within the meaning and range of equivalents of the claims are therefore intended to be embraced therein.

What is claimed is:

1. A surgical product of the type which is folded to be packaged and subsequently radiation sterilized, comprising a moisture absorbent web of fibrous sheet material having a binder present on said surface in a first given pattern so that fibers of said material are exposed at given areas adjacent said first given pattern, and a release agent applied to said surface in a second lattice-like given pattern which overlies a portion of said binder and a portion of said fibers exposed at said given areas.

2. The product of claim 1, wherein said release agent comprises silicone.

3. A packaged sterile surgical product comprising a moisture absorbent folded web of fibrous sheet material having a binder present on contiguous folded surfaces of said material in a first given pattern so that fibers of said material are exposed at given areas adjacent said first given pattern, and a release agent applied to said surfaces in a second lattice-like pattern which overlies a portion of said binder and a portion of each of said fibers exposed at said given areas, said packaged product being sterilized by exposure thereof to radiation.

4. The packaged product of claim 3, wherein said release agent comprises silicone.

5. The packaged product of claim 4, wherein said second given pattern of release agent overlies from about 15 to about 18 percent of the first given pattern of said binder.

* * * * *